US009057778B2

(12) United States Patent
Gurton et al.

(10) Patent No.: US 9,057,778 B2
(45) Date of Patent: Jun. 16, 2015

(54) REMOTE SENSING USING COHERENT SONIC WAVE PHOTOACOUSTIC DETECTION AND METHODS

(71) Applicant: U.S. Army Research Laboratory, Adelphi, MD (US)

(72) Inventors: Kristan Peter Gurton, Olney, MD (US); Yongle Pan, Cheshire, CT (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 352 days.

(21) Appl. No.: 13/693,367

(22) Filed: Dec. 4, 2012

(65) Prior Publication Data
US 2014/0150529 A1 Jun. 5, 2014

(51) Int. Cl.
  *G01N 21/17* (2006.01)
  *G01S 17/02* (2006.01)
  *G01S 15/74* (2006.01)

(52) U.S. Cl.
  CPC ........... *G01S 17/023* (2013.01); *G01N 21/1702* (2013.01); *G01S 15/74* (2013.01)

(58) Field of Classification Search
  CPC ....................... G01N 21/1702; G01N 21/1704
  USPC ........................................................ 73/24.02
  See application file for complete search history.

(56) References Cited

PUBLICATIONS

Harata, H Nishimura, T Sawada," Laser-induced surface acoustic waves and photothermal surface gratings generated by crossing two pulsed laser beams", Appl. Phys. Let. vol. 57, (1990).

Schneider, D., et al., "Non-destructive evaluation of diamond and diamond-like carbon films by laser induced surface acoustic waves," Thin solid Films, vol. 295, pp. 107-116, (1997).
Sabsabi, M., et al. "Quantitative Analysis of Aluminum Alloys by Laser-Induced Breakdown Spectroscopy and Plasma Characterization" Applied Spectroscopy, vol. 49, No. 4 pp. 499-507. (1995).
Tognoni, E., et al. "Quantitative micro-analysis by laser-induced breakdown spectroscopy: a review of the experimental approaches," Spectrochimica Acta Part B 57 (2002) pp. 1115-1130.
Radziemski, L., et al. "Time-Resolved Laser-Induced Breakdown Spectrometry of Aerosols," Anal. Chem. 55, pp. 1246-1252 (1983).
Wynn, C.M., et al. "Dynamic photoacoustic spectroscopy for trace gas detection," Applied Physics Letters 101, 184103 (2012); doi: 10.1063/1.4764515.

*Primary Examiner* — John Chapman, Jr.
(74) *Attorney, Agent, or Firm* — Lawrence E. Anderson

(57) ABSTRACT

A method and system for detecting composition of a physical space comprising: a laser beam source; an acoustic sensor; a beam focusing mechanism for focusing the laser beam at predetermined points in the physical space to generate a thermal inhomogeneity which results in the propagation of a pressure wave that propagates outward from the predetermined excitation point at a propagation velocity approximating the speed of sound for the particular composition of the media; at least one processor for controlling the timing for the laser beam focusing to generate thermal inhomogeneities; whereby the laser focal point is moved sequentially along the light-of-sight at various excitation points by the beam focusing mechanism approximately at the phase front velocity to define a series of predetermined excitation points and pressure wave propagations such that the series of pressure wave propagations combine to produce a coherent pressure wave detectable by the acoustic sensor.

18 Claims, 3 Drawing Sheets

REMOTE SENSING USING COHERENT SONIC WAVE PHOTOACOUSTIC DETECTION AND METHODS

STATEMENT OF GOVERNMENT INTEREST

The invention described herein may be manufactured, used, and licensed by or for the United States Government without the payment of royalties thereon.

BACKGROUND OF THE INVENTION

A body of research has been conducted in which lasers are used to induced phase-change (create a plasma) on solid surfaces and in gases, in order to deduce atomic related spectral information, i.e., laser induced breakdown spectroscopy. Similarly, there is a body of research in which practitioners have used laser illumination to generate acoustic surface waves, in which Fourier analysis is applied to the acoustic signal, in order to measure non-destructively various physical parameters. See for example, A Harata, H Nishimura, T Sawada, "Laser-induced surface acoustic waves and photo-thermal surface gratings generated by crossing two pulsed laser beams", App. Phys. Let. Vol. 57, (1990) and D Schneider, T Schwarz, H J Scheibe, M Panzner, "Non-destructive evaluation of diamond and diamond-like carbon films by laser induced surface acoustic waves. Thin solid films, vol. 295, pp. 107-116, (1997), both of which are hereby incorporated by reference.

On methodology for detection involves an experimental technique termed optical Light Detection And Ranging, (LIDAR). LIDAR methods, techniques, and instrumentation is a fairly mature and established technique which has proven effective in measuring 3D wind profiles. To a lesser degree there are claims of being able to measure various elemental atmospheric gas components, water vapor, temperature, and other atmospheric parameters. However, such claims are premised on assumptions that that may, or may not be accurate, and these assumptions greatly affect LIDAR derived results, e.g., most LIDAR predictions involve an inverse process that requires important information about aerosol size distribution, shape, and composition, which is rarely known with any degree of accuracy. The main limitation with the LIDAR approach is that it can only measure a parameter called optical backscatter which is a complex function of many phenomena. For example, generally speaking, an optical LIDAR propagates a pulse of energy at a particular wavelength through the atmosphere. As the pulse propagates it undergoes attenuation by aerosol scattering, aerosol absorption, and gaseous absorption (neglecting molecular scattering). A fraction of the original pulse is scattered back (backscattered) to the transmission point, and is detected by an optical detector. The backscatter is effectively the ratio of the power sent out to the power scattered back to the receiver. However, to make use of this type of measurement, practitioners must make important assumptions as mentioned above because atmospheric backscatter is a complex function of both scattering and absorption.

SUMMARY OF THE INVENTION

A preferred method for detecting the composition of a physical space comprises:

at a first predetermined time focusing a laser at a first predetermined excitation point along the line of sight of the laser to create rapid localized heating of the gases to produce a thermal inhomogeneity which results in the propagation of a first pressure wave; the first pressure-wave propagating outward from the predetermined excitation point at a propagation velocity approximating the speed of sound that is defined for the particular composition of the media; at a second predetermine time focusing a laser to a second predetermined excitation point along the line of sight of the laser to produce a second pressure wave; the velocity from the first predetermined excitation point to the second predetermined excitation point being selected to approximate the propagation velocity of the pressure wave which creates an effective superposition of the first and second pressure-waves at the second predetermined excitation point: and moving, the laser focal point sequentially along the light-of-sight at various excitation points approximately at the phase front velocity to define a series of predetermined excitation points and pressure wave propagations: whereby the series of pressure wave propagations combine to produce a coherent pressure wave that can be detected at a predetermined distance by an appropriate acoustic sensor.

Optionally, the method further includes returning the laser focus to the first predetermined excitation point whereupon the process is then repeated along the laser beam line-of-sight until a coherent pressure wave is produced that can be detected at a predetermined distance by an appropriate acoustic sensor.

Optionally, each sweep from the first predetermined excitation point to the last predetermined excitation point may be repeated at a fixed frequency F, defined by the inverse of the time period needed to move from the first predetermined excitation point to the last in the series of excitation points at the propagation velocity.

Optionally, the shockwave may be detected by an acoustic receiving sensor mounted in the proximity of the laser beam source.

Optionally, the absorption spectra for localized regions of the atmosphere may be detected by an acoustical sensor and measured by at least one processor.

Optionally, the method may be utilized for the detection of hazardous chemical/airborne materials and/or gases in the atmosphere. Also, as an option a Cassegrain telescope configuration may be utilized, and/or the coherent pressure wave may be received by a sensor positioned approximately on the central axis of the laser beam. As another option the method is used in conjunction with a lidar system. As a further option, the method may be capable of remotely measuring atmospheric absorption related parameters for identifying the biological/chemical composition of the atmosphere at the physical space.

A preferred embodiment system for detecting the composition of a physical space comprises a laser beam source; an acoustic sensor; a beam focusing mechanism for focusing the laser beam at predetermined points in the physical space to generate a thermal inhomogeneity which results in the propagation of a pressure wave; the pressure-wave propagating outward from the predetermined excitation point at a propagation velocity approximating the speed of sound that is defined for the particular composition of the media; at least one processor for controlling the timing for the laser beam focusing to generate thermal inhomogeneities: whereby the laser focal point is moved sequentially along the light-of-sight at various excitation points by the beam focusing mechanism approximately at the phase front velocity to define a series of predetermined excitation points and pressure wave propagations such that the series of pressure wave propagations combine to produce a coherent pressure wave that can be detected at a predetermined distance by the acoustic sensor.

As an option, the laser may be capable of being dynamically focused at any point within the physical space by the beam focusing mechanism under the control of the at least one processor. Optionally, the beam focusing mechanism may have a Cassegrain telescope configuration. Optionally, the at least one processor may operate to generate the thermal inhomogeneities at time intervals such that at a first predetermined time the laser beam is focused at a first predetermined excitation point along the line of sight of the laser to create rapid localized heating of the gases to produce a thermal inhomogeneity which results in the propagation of a first pressure wave; the first pressure-wave propagating outward from the predetermined excitation point at a propagation velocity approximating the speed of sound that is defined for the particular composition of the media; and at a second predetermine time the laser beam is focused to a second predetermined excitation point along the line of sight of the laser to produce a second pressure wave; the velocity from the first predetermined excitation point to the second predetermined excitation point being selected to approximate the propagation velocity of the pressure wave which creates an effective superposition of the first and second pressure-waves at the second predetermined excitation point; and wherein the laser focal point is moved sequentially along the light-of-sight at various excitation points approximately at the phase front velocity to define a series of predetermined excitation points and pressure wave propagations such that the summation of the pressure waves produces a coherent pressure wave that is detected by the acoustic sensor.

Optionally, the at least one processor may operate to repeat each cycle from the first predetermined excitation point to the last predetermined excitation point at a fixed frequency F, defined by the inverse of the time period needed to move from the first predetermined excitation point to the last in the series of excitation points at the propagation velocity. As another option, the system may operate in conjunction with or include a Lidar system.

The system may optionally include a sensor which receives the coherent pressure wave that is positioned approximately on the central axis of the laser beam. As a further option, the laser beam is emitted in the direction of the line-of-sight along an axis and the propagation and sensing of the acoustic waves are conducted along the axis.

BRIEF DESCRIPTION OF THE DRAWINGS

The foregoing and other objects, features, and advantages of the invention will be apparent from the following more detailed description of the preferred embodiments of the invention, as illustrated in the accompanying drawings, wherein.

Figure 1:
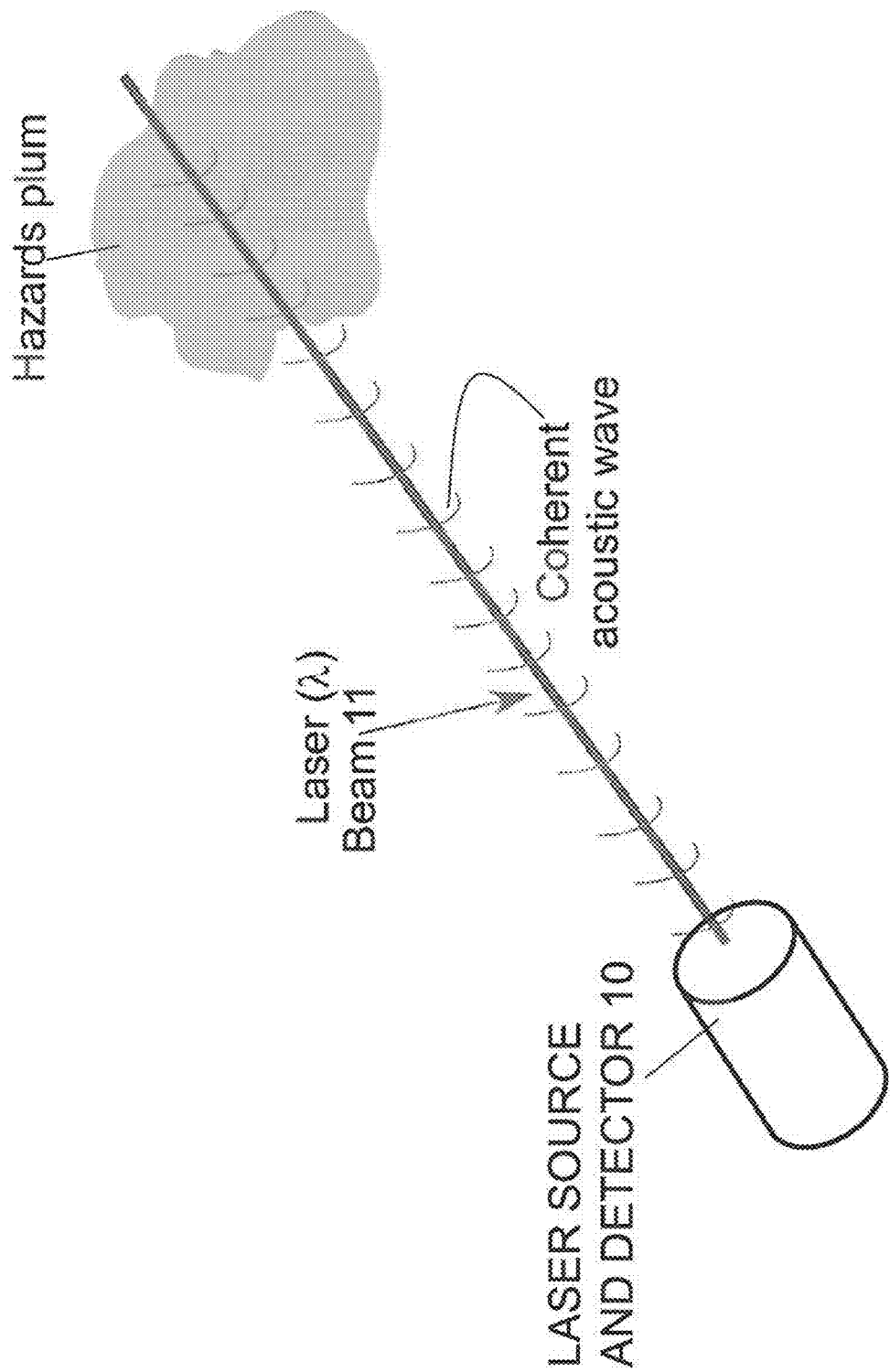
FIG. 1 is a diagrammatic view of represents a preferred embodiment showing a laser source and detector 10 emitting a laser beam 11 and receiving an acoustic wave indicative of the chemical composition of the hazards plum.

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximates.

DESCRIPTION OF THE PREFERRED EMBODIMENTS

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention. Rather, these embodiments are provided so that this disclosure will be thorough and complete, and will fully convey the scope of the invention to those skilled in the art. In the drawings, the dimensions of objects and regions may be exaggerated for clarity. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element such as an object, layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It will be understood that, although the terms first, second, etc. may be used herein to describe various elements, components, regions, layers and/or sections, these elements, components, regions, layers and/or sections should not be limited b these terms. For example, when referring first and second elements, these terms are only used to distinguish one element, component, region, layer or section from another region, layer or section. Thus, a lust element, component, region, layer or section discussed below could be termed a second element, component, region, layer or section without departing from the teachings of the present invention.

Embodiments of the present invention are described herein with reference to cross-section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

Unless otherwise defined, all terms (including technical and Scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will also be appreciated by those of skill in the art that references to a structure or feature that is disposed "adjacent" another feature may have portions that overlap or underlie the adjacent feature.

Referring to FIG. 1, the methodology of a preferred embodiment of the present invention comprises employing a method to measure an absorption "only" related parameter in the atmosphere at a distance (i.e., remotely). The method and system is based on a phenomena referred to as Coherent Sonic Wave Photoacoustic Spectroscopy (CSWPS). The fundamental concept is as follows. A laser operating at wavelength A., is propagated through free space that contains optically absorbing, atmospheric gases, aerosols, particulate matter, hydrosols, etc (see FIG. 1). The Coherent Sonic Wave Photoacoustic Spectroscopy (CSWPS) technique is applicable for both continues-wave (CW) and pulsed laser sources $10$, $25$. In FIG. 1, the element $10$ comprises both the transmitting laser and the acoustical receiver. The laser $10$, can be dynamically, focused at any point along the propagation path. For our example, a Cassegrain telescope $20$ can be utilized with an adaptive secondary mirror $23$, as shown in FIG. 2A, in order to operate as a laser beam focusing mechanism. Laser $25$ emits a beam and the diameter of the expanded laser beam at the exit aperture may be defined as D (See FIG. 2B). The laser beam operation may optionally be controlled by a processor $26$. The distance from the telescope $20$ to a distant point in spaces be may be defined as $X1$, such that the ratio of $D/X1$ is very small. i.e., $D/X1 \gg 1$. At time $T1$ the laser is focused at a point in space, $X1$ (see FIGS. 2A and 3 (beginning at time $T1$)). A portion of the focused laser energy is absorbed by the gas/aerosol media which in turns produces localized heating in a small region about, point, $X1$. This rapid localized heating produces a thermal inhomogeneity is the media about the laser focal point, which results in the production of a pressure wave. This pressure-wave propagates outward from the excitation point, $X1$, at velocities at, or about, the speed of sound, $V_s$, that is defined for the particular gas/aerosol media. At some later time, $T2$, the pressure-wave from excitation point, $X1$, will have expanded to a radius, $R2$, as shown by the circle $X1_{T2}$ in FIG. 3, (Time T2). At time, $T2$, the laser focus is translated, to a position, $X2$ (shown as the dot labeled $X2_{T2}$ in FIG. 3 at Time T2), along the line-of-sight (LOS), which produces a second pressure (shock) wave at $X2$.

The movement (velocity) of the laser focal point, from point $X1$ to $X2$ is judiciously chosen to match the phase front velocity, $V_s$. This creates an effective superposition (summation) of the two pressure-waves at point $X2$. The process is continued by moving the laser focal point along the light-of-sight (LOS) at the velocity $V_s$, defining a continuous series of points $X1$, $X2$, $X3$ ... $X_f$, where $X_f$ is that last location along the LOS, and $T1$, $T2$, $T3$ ... $T_f$ are the time periods at which each corresponding position are obtained. At the last position point, $X_f$, at time, $T_f$, along the LOS (preferably in the direction towards the acoustic or pressure-wave detector) the laser sources is switched off. At this point the dynamic focal system reverts to the initial condition necessary to produce a focused laser beam back at location $X1$. The process then continuously repeated along points $X1$, $X2$, $X3$ ... $X_f$, (see FIG. 3, Times T3 and Tf) producing a large coherent pressure (shock) wave that can be detected at great distances by an appropriate acoustic sensor.

Figure 2:
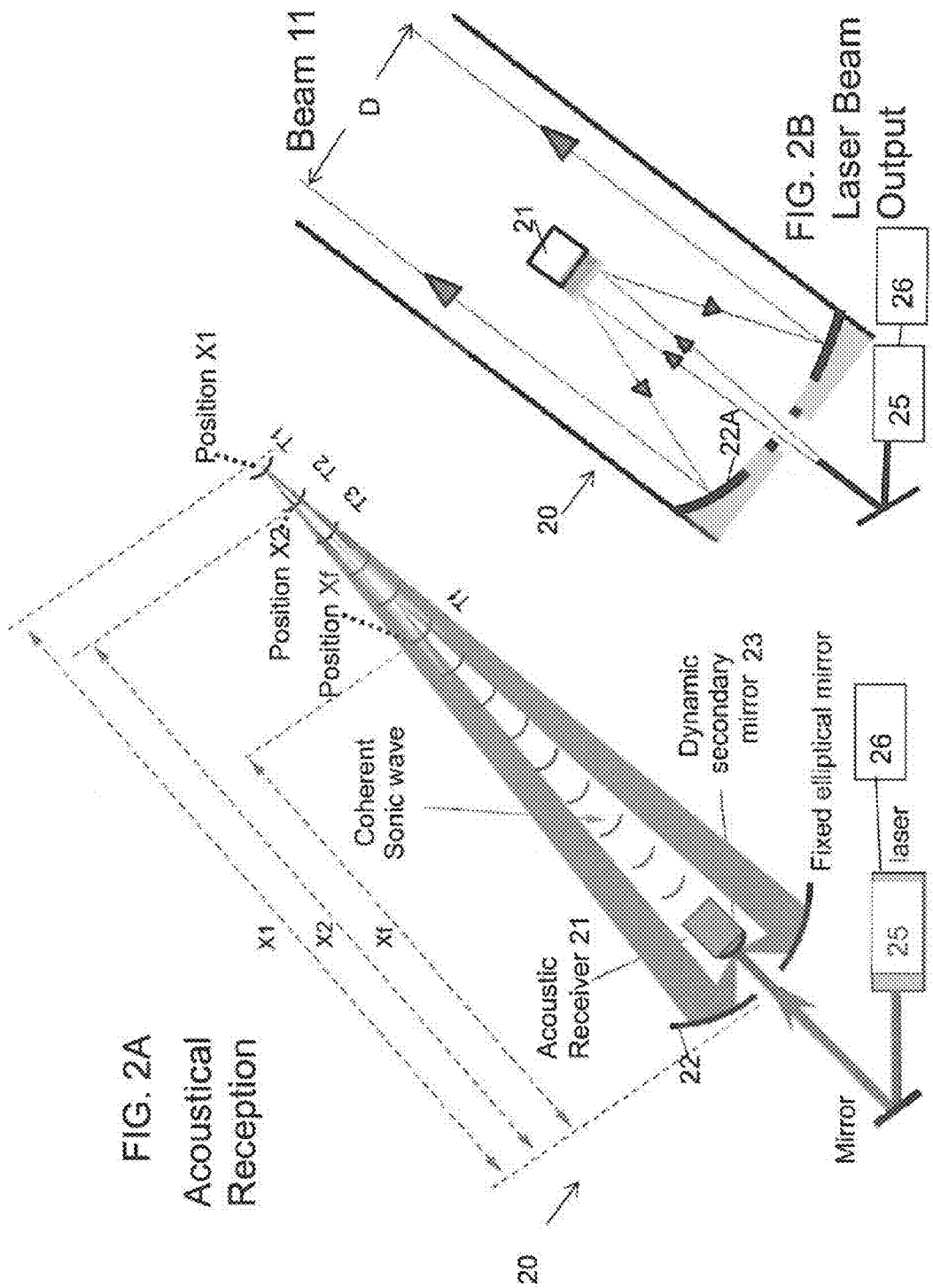
FIG. 2A is a schematic illustration showing a preferred embodiment Cassegrain telescope 20 assembly and acoustical wave generation.
FIG. 2B is an enlarged schematic illustration showing one particular embodiment involving a Cassegrain telescope 20 assembly of FIG. 2A further illustrating laser beam generation.
Figure 3:
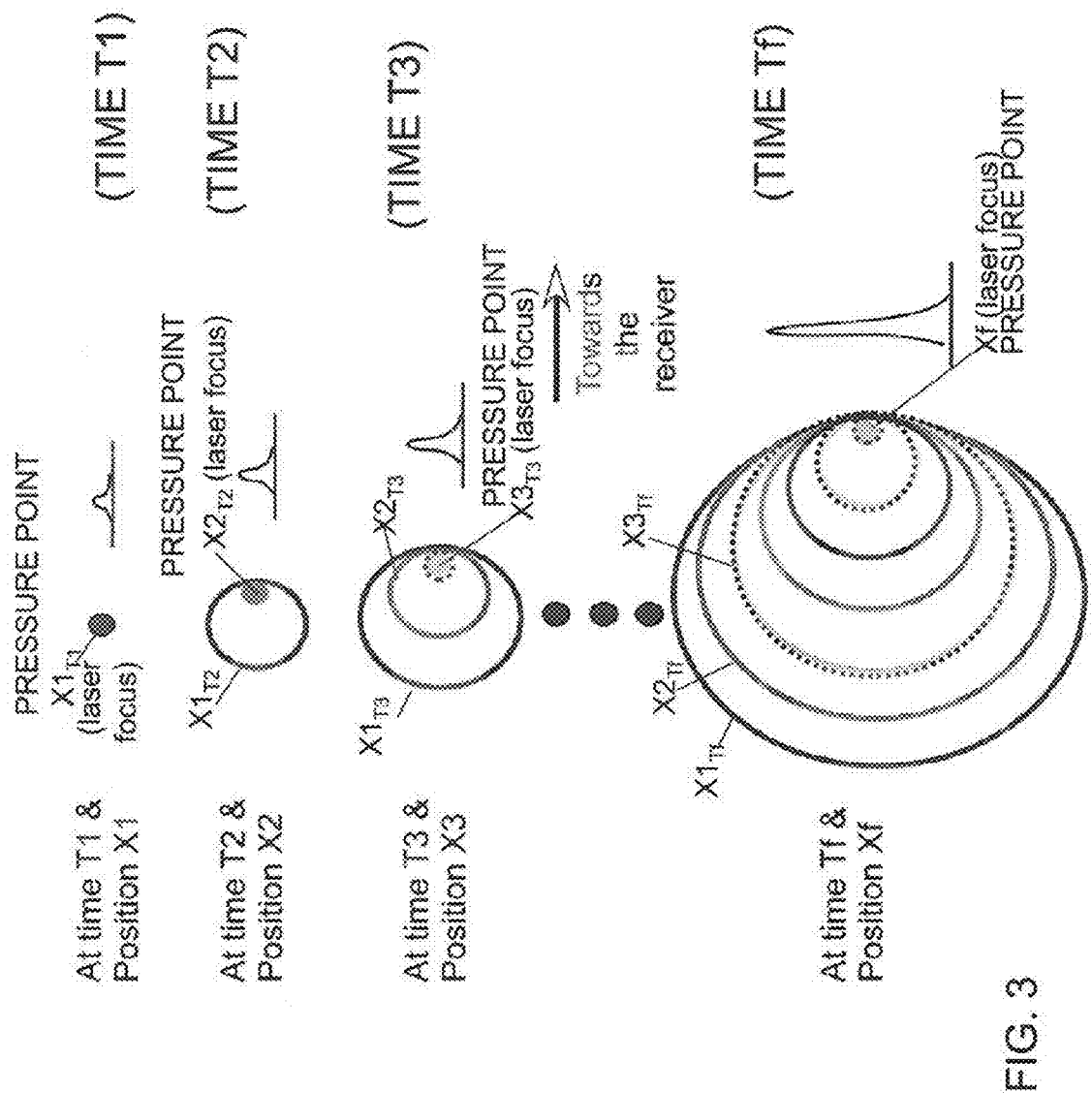
FIG. 3 is a diagrammatic illustration showing sequential development of pressure induced waves according to a preferred methodology of the present invention.

The repetition of each sweep is conducted at a fixed frequency F, defined by the inverse of the time period needed to complete one complete sweep, i.e., the time period required to sweep the laser focal point through a distance $|X1 \cdot X_f|$ and back to location $X1$. The magnitude of the shockwave is detected by an acoustic receiving sensor conveniently mounted opposite to dynamic secondary mirror located in the telescope, as shown in FIG. 2. In order to optimize the signal-to-noise, (S/N), of the recorded acoustic signal (at a cycle frequency, F) phase sensitive amplification and/or time-gating is used to filter out spurious ambient acoustic noise. Because $D/X1 \gg 1$, the geometry, intensity, and volumetric extent of each focal point, is approximately the same, lending to continuity between all excitation points. The intensity/magnitude of the resultant acoustic wave that is recorded by the acoustic sensor is directly related to the optical absorption of the gas/aerosol media. It is preferable, but not critical that the path/motion for each successive excitation point be moving in the direction towards the acoustic sensor. The process is repetitive at frequency, F, as defined by the inverse of period between the first excitation at time, $T1$, and the last exaction at time, $T_f$, (shown in FIG. 2). By tuning the laser source over different wavelengths, $1.1$, $J.2$, $13$ etc., one can effectively measure an absorption related spectra (tunable laser source shown in FIG. 2). In spectral regions in which the atmospheric optical attenuation is present, a correction using standard atmospheric transmission models may be applied to the raw absorption spectra. This absorption related spectra can be used as an identifiable metric for the detection of pre-described atmospheric gaseous, aerosol, and particulate mixtures. By using a pulsed-laser source one can define the geometry, size and extent, of a particular gaseous/aerosol species. Because the temporal response between a gas and an aerosol are different, i.e., optical energy is absorbed and transferred to thermal energy nearly instantaneously for gas, whereas the same process may take micro to milliseconds for aerosols (depending on aerosol size and composition). Therefore by reducing the laser pulse width to a sufficiently small period, one can separate gaseous absorption from aerosol absorption, thus significantly improving information content inherent in the described CSWPS method.

Unlike LIDAR, the Coherent Sonic Wave Photoacoustic Spectroscopy (CSWPS) approach of the present invention effectively measures only the atmospheric absorption and would not rely on questionable assumptions about the composition of the atmosphere, it is a direct In situ measurement. Moreover, the CSWPS method of the present invention may be complimentary with the established LIDAR method, and because the required instrumentation for both approaches are very similar ... established LIDAR systems could be easily be modified to conduct both techniques simultaneously and in effect simultaneously measure atmospheric absorption, backscatter, and total extinction characteristics. This would greatly increase the information content, accuracy and nature, of the atmospheric measurement information currently in circulation.

As described above, a preferred embodiment may be used for improved atmospheric remote sensing, and in particular the remote detection and identification of toxic/harmful release of chemical or biological warfare agents. Additional, applications would involve commercial monitoring of manmade and naturally occurring pollutants. Similarly, there is great debate involving global warming/climate change in which remote sensing of the atmosphere will continue to be of great importance. As a result, the introduction of a new remote atmospheric spectroscopic approach, i.e., the present invention Coherent Sonic Wave Photoacoustic Spectroscopy (CSWPS), would be of great importance.

Besides remote atmospheric absorption spectroscopy, since the method inherently produces an effective pressure-wave (shock wave) whose position and direction can be controlled from a distance, it is conceivable that the present invention methodology may have application(s) in the rapidly emerging unmanned aerial vehicle (UAV) area.

The preferred embodiments of the present invention provide remote in situ, measure of electromagnet (EM) absorption within a predefined volume of the atmosphere. The preferred embodiment provide for optical generation of a pressure/acoustic wave of sufficient energy capable of detection at a distance. This is achieved by the judicious movement at a specific velocity of a region in space in which electromagnet (EM) radiation is brought to a focus. The intense focusing of EM energy results in rapid localized heating of the atmospheric media producing a spherically outgoing pressure-wave (see FIG. 3). The focal point is moved along a predescribed linear path, such that the velocity of the movement of the focused energy point(s) exactly/notches the velocity of the phase front for each resulting pressure-wave (usually this velocity will be close to, if not identical to the speed of sound, see FIG. 3 at Time T2). By matching the velocity of the dynamically moving focal points with that of the outgoing spherical pressure-wave phase front, one creates a coherent superposition (summation) of many pressure-waves resulting in a large acoustic front that is of sufficiently intensity (see FIG. 3 at times T3 and T(f). The sufficiently large resultant acoustic signal is detected over long distances using current acoustic detection schemes, i.e., phase sensitive detection and amplification, and/or time gating the acoustic sensor integration period.

The magnitude of the received/recorded acoustic signal is directly related to the optical absorption of the probe medium (atmosphere) for the specific wavelength of the propagated EM energy. Multiple wavelengths can be generated sequentially, which are subsequently propagated such that an absorption profile extending over many wavelengths can be determined, i.e., an in situ measure of the absorption spectra.

The present invention provides for reliable means for the "remote" detection of hazardous airborne chemical/biological warfare agents. Current state-of-art involves a laser propagation technique, called Light Detection and Ranging (LIDAR), which to date, has proven ineffective. A preferred methodology of the present invention provides a method capable of remotely measuring, in situ, an atmospheric absorption related parameter(s) that will prove more effective in identifying the biological/chemical composition of the atmosphere. The preferred methodology is based on a phenomena referred to as "Coherent Sonic Wave Photoacoustic Spectroscopy" (CSWPS), which is capable of determining atmospheric absorption. The main limitation with the LIDAR approach is that it can only measure a single (fairly nondescript) parameter called optical backscatter, which is often a complex function of many phenomena. Unlike LIDAR, the CSWPS approach directly measures the optical absorption (an ability that is currently unavailable) which is direct function of the molecular composition of the media. By operating the described CSWPS methodology of a preferred embodiment in a multi-wavelength mode, one can remotely measure the absorption spectra, for localized regions of the atmosphere. The resultant spectra may prove to be an effective identifier appropriate for the detection of hazardous chemical/biological airborne materials and/or gases. In addition, we foresee the CSWPS method to be complimentary with the established LIDAR method, and because the required instrumentation for both approaches are very similar, established LIDAR systems could easily be modified to conduct both.

As used herein the terminology "physical space" includes, the region within a chamber, the earth's atmosphere, outer space, an undefined region or the like.

Obviously, many modifications and variations of the present invention are possible in light of the above teachings. It is therefore to be understood that, within the scope of the appended claims, the invention many be practiced otherwise than as specifically described.

What is claimed is:

1. A method for detecting the composition of a physical space comprising;
   at a first predetermined time focusing a laser at a first predetermined excitation point along the line of sight of the laser to create rapid localized heating of the gases to produce a thermal inhomogeneity which results in the propagation of a first pressure wave; the first pressure-wave propagating outward from the predetermined excitation point at a propagation velocity approximating the speed of sound that is defined for the particular composition of the media;
   at a second predetermine time focusing a laser to a second predetermined excitation point along the line of sight of the laser to produce a second pressure wave; the velocity from the first predetermined excitation point to the second predetermined excitation point being selected to approximate the propagation velocity of the pressure wave which creates an effective superposition of the first and second pressure-waves at the second predetermined excitation point; and
   moving the laser focal point sequentially along the light-of-sight at various excitation points approximately at the phase front velocity to define a series of predetermined excitation points and pressure wave propagations;
   whereby the series of pressure wave propagations combine to produce a coherent pressure wave that can be detected at a predetermined distance by an appropriate acoustic sensor.

2. The method of claim 1 further including returning the laser focus to the first predetermined excitation point whereupon the process is then repeated along the laser beam line-of-sight until a coherent pressure wave is produced that can be detected at a predetermined distance by an appropriate acoustic sensor.

3. The method of claim 2 wherein the repetition of each sweep from the first predetermined excitation point to the last predetermined excitation point is conducted at a fixed frequency F, defined by the inverse of the time period needed to move from the first predetermined excitation point to the last in the series of excitation points at the propagation velocity.

4. The method of claim 1 wherein the pressure wave is detected by an acoustic receiving sensor mounted in the proximity of the laser beam source 5. The method of claim 1 wherein the absorption spectra for localized regions of the atmosphere are detected by an acoustical sensor and measured by at least one processor.

6. The method of claim 1 wherein the method is utilized for the detection of hazardous chemical/biological airborne materials and/or gases in the atmosphere.

7. The method of clam 1 wherein the coherent pressure wave is detected using a Cassegrain telescope configuration.

8. The method of claim 7 wherein the coherent pressure wave is received by a sensor positioned approximately on the central axis of the laser beam.

9. The method of claim 1 wherein the method is used in conjunction with a lidar system.

10. The method of claim 1 wherein the method is capable of remotely measuring atmospheric absorption related parameters for identifying the biological/chemical composition of the atmosphere at the physical space.

11. A system for detecting the composition of a physical space comprising:
a laser beam source;
an acoustic sensor;
a beam focusing mechanism for focusing the laser beam at predetermined points in the physical space to generate a thermal inhomogeneity which results in the propagation of a pressure wave; the pressure-wave propagating outward from the predetermined excitation point at a propagation velocity approximating the speed of sound that is defined for the particular composition of the media;
at least one processor for controlling the timing for the laser beam focusing to generate thermal inhomogeneities;
whereby the laser focal point is moved sequentially along the light-of-sight at various excitation points by the beam focusing mechanism approximately at the phase front velocity to define a series of predetermined excitation points and pressure wave propagations such that the series of pressure wave propagations combine to produce a coherent pressure wave that can be detected at a predetermined distance by the acoustic sensor.

12. The system of claim 11 wherein the laser can be dynamically focused at any point within the physical space by the beam focusing mechanism under the control of the at least one processor.

13. The system of claim 11 wherein the beam focusing mechanism comprises a Cassegrain telescope configuration.

14. The system of claim 11 wherein the at least one processor operates to generate the thermal inhomogeneities at time intervals such that at a first predetermined time the laser beam is focused at a first predetermined excitation point along the line of sight of the laser to create rapid localized heating of the gases to produce a thermal inhomogeneity which results in the propagation of a first pressure wave; the first pressure-wave propagating outward from the predetermined excitation point at a propagation velocity approximating the speed of sound that is defined for the particular composition of the media; and at a second predetermine time the laser beam is focused to a second predetermined excitation point along the line of sight of the laser to produce a second pressure wave; the velocity from the first predetermined excitation point to the second predetermined excitation point being selected to approximate the propagation velocity of the pressure wave which creates an effective superposition of the first and second pressure-waves at the second predetermined excitation point; and wherein the laser focal point is moved sequentially along the light-of-sight at various excitation points approximately at the phase front velocity to define a series of predetermined excitation points and pressure wave propagations such that the summation of the pressure waves produces a coherent pressure wave that is detected by the acoustic sensor.

15. The system of claim 11 wherein the at least one processor operates to repeat each cycle from the first predetermined excitation point to the last predetermined excitation point at a fixed frequency F, defined by the inverse of the time period needed to move from the first predetermined excitation point to the last in the series of excitation points at the propagation velocity.

16. The system of claim 11 further comprising a lidar system.

17. The system of claim 11 wherein the coherent pressure wave is received by a sensor positioned approximately on the central axis of the laser beam.

18. The system of claim 11 wherein the laser beam is emitted in the direction of the line-of-sight along an axis and the propagation and sensing of the acoustic waves are conducted along the axis.

* * * * *